United States Patent
Sharma et al.

(10) Patent No.: US 7,655,658 B2
(45) Date of Patent: Feb. 2, 2010

(54) THIENO [2,3-D]PYRIMIDINE-2,4-DIONE MELANOCORTIN-SPECIFIC COMPOUNDS

(75) Inventors: Shubh D. Sharma, Cranbury, NJ (US); Yiqun Shi, East Brunswick, NJ (US)

(73) Assignee: Palatin Technologies, Inc., Cranbury, NJ (US)

(*) Notice: Subject to any disclaimer, the term of this patent is extended or adjusted under 35 U.S.C. 154(b) by 537 days.

(21) Appl. No.: 11/040,838

(22) Filed: Jan. 21, 2005

(65) Prior Publication Data
US 2005/0124636 A1 Jun. 9, 2005

Related U.S. Application Data

(63) Continuation-in-part of application No. 10/837,519, filed on Apr. 30, 2004, now Pat. No. 7,456,184, and a continuation-in-part of application No. 10/762,079, filed on Jan. 21, 2004, now Pat. No. 7,354,923, and a continuation-in-part of application No. 10/761,889, filed on Jan. 21, 2004, now Pat. No. 7,326,707, said application No. 10/762,079 and a continuation-in-part of application No. PCT/US02/25574, filed on Aug. 12, 2002.

(60) Provisional application No. 60/538,100, filed on Jan. 21, 2004, provisional application No. 60/474,497, filed on May 30, 2003, provisional application No. 60/441,139, filed on Jan. 17, 2003, provisional application No. 60/311,404, filed on Aug. 10, 2001, provisional application No. 60/546,393, filed on Feb. 19, 2004, provisional application No. 60/467,442, filed on May 1, 2003.

(51) Int. Cl.
*A61K 31/497* (2006.01)
*C07D 241/36* (2006.01)

(52) U.S. Cl. .................. 514/252.13; 544/349
(58) Field of Classification Search ............. 544/349; 514/252.13
See application file for complete search history.

(56) References Cited

U.S. PATENT DOCUMENTS

| | | | |
|---|---|---|---|
| 4,148,923 A | 4/1979 | Giudicelli et al. |
| 4,239,763 A | 12/1980 | Milavec et al. |
| 4,626,549 A | 12/1986 | Molloy et al. |
| 4,680,289 A | 7/1987 | Applezweig |
| 4,711,957 A | 12/1987 | Lai |
| 4,766,125 A | 8/1988 | Van Daele |
| 4,937,267 A | 6/1990 | Holloway et al. |
| 4,938,763 A | 7/1990 | Dunn et al. |
| 4,943,578 A | 7/1990 | Naylor et al. |
| 4,968,684 A | 11/1990 | Van Daele et al. |
| 4,997,836 A | 3/1991 | Sugihara et al. |
| 5,120,713 A | 6/1992 | Mugica |
| 5,292,726 A | 3/1994 | Ashton et al. |
| 5,331,573 A | 7/1994 | Balaji et al. |
| 5,334,830 A | 8/1994 | Fukuyama et al. |
| 5,348,955 A | 9/1994 | Greenlee et al. |
| 5,464,788 A | 11/1995 | Bock et al. |
| 5,494,919 A | 2/1996 | Morriello et al. |
| 5,550,131 A | 8/1996 | Sugihara et al. |
| 5,574,031 A | 11/1996 | Abramo et al. |
| 5,579,250 A | 11/1996 | Balaji et al. |
| 5,599,809 A | 2/1997 | Hickey et al. |
| 5,639,778 A | 6/1997 | Andersson et al. |
| 5,672,602 A | 9/1997 | Burkholder et al. |
| 5,721,250 A | 2/1998 | Morriello et al. |
| 5,721,251 A | 2/1998 | Chen et al. |
| 5,736,539 A | 4/1998 | Graham et al. |
| 5,753,445 A | 5/1998 | Fillit et al. |
| 5,753,653 A | 5/1998 | Bender et al. |
| 5,763,445 A | 6/1998 | Kruse et al. |
| 5,798,359 A | 8/1998 | Shue et al. |
| 5,804,578 A | 9/1998 | Chakravarty et al. |
| 5,856,326 A | 1/1999 | Anthony et al. |
| 5,872,262 A | 2/1999 | Dolle et al. |
| 5,877,182 A | 3/1999 | Nargund et al. |
| 5,880,125 A | 3/1999 | Nargund |
| 5,880,128 A | 3/1999 | Doll et al. |
| 5,891,418 A | 4/1999 | Sharma |
| 5,892,038 A | 4/1999 | Dolle et al. |
| 5,936,089 A | 8/1999 | Carpino et al. |
| 5,965,565 A | 10/1999 | Chen et al. |

(Continued)

FOREIGN PATENT DOCUMENTS

WO    WO 96/38471    12/1996

(Continued)

OTHER PUBLICATIONS

*Synthetic Peptides: A User's Guide*, GA Grant, editor, W.H. Freeman & Co., New York, 1992, the teachings of which are incorporated herein by reference, including the text and table set forth at pp. 11 through 24.

(Continued)

*Primary Examiner*—James O Wilson
*Assistant Examiner*—Ebenezer Sackey
(74) *Attorney, Agent, or Firm*—Stephen A. Slusher

(57) ABSTRACT

A thienopyrimidine compound of the formula:

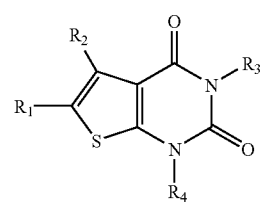

wherein $R_1$, $R_2$, $R_3$, and $R_4$ are as defined herein, and methods of use of such compounds for the treatment of melanocortin receptor-associated disorders.

15 Claims, No Drawings

U.S. PATENT DOCUMENTS

| | | | |
|---|---|---|---|
| 5,968,938 | A | 10/1999 | Williams et al. |
| 6,020,334 | A | 2/2000 | Fukushi et al. |
| 6,027,711 | A | 2/2000 | Sharma |
| 6,033,656 | A | 3/2000 | Mikami et al. |
| 6,127,381 | A | 10/2000 | Basu et al. |
| 6,127,424 | A | 10/2000 | Martin et al. |
| 6,140,354 | A | 10/2000 | Dax et al. |
| 6,162,805 | A | 12/2000 | Hefti |
| 6,191,117 | B1 | 2/2001 | Kozachuk |
| 6,207,665 | B1 | 3/2001 | Bauman et al. |
| 6,207,699 | B1 | 3/2001 | Rothman |
| 6,214,831 | B1 | 4/2001 | Yokoo et al. |
| 6,245,764 | B1 | 6/2001 | Kahn et al. |
| 6,284,735 | B1 | 9/2001 | Girten et al. |
| 6,294,539 | B1 | 9/2001 | Lou et al. |
| 6,303,611 | B1 | 10/2001 | Zhang et al. |
| 6,316,470 | B1 | 11/2001 | Kover et al. |
| 6,331,285 | B1 | 12/2001 | Sharma |
| 6,340,868 | B1 | 1/2002 | Lys et al. |
| 6,350,760 | B1 | 2/2002 | Bakshi et al. |
| 6,372,747 | B1 | 4/2002 | Taveras et al. |
| 6,376,509 | B1 | 4/2002 | Bakshi et al. |
| 6,410,548 | B2 | 6/2002 | Nargund et al. |
| 6,432,438 | B1 | 8/2002 | Shukla |
| 6,432,959 | B1 | 8/2002 | Cooper et al. |
| 6,451,783 | B1 | 9/2002 | Hadcock et al. |
| 6,458,789 | B1 | 10/2002 | Forood et al. |
| 6,458,790 | B2 | 10/2002 | Palucki et al. |
| 6,469,006 | B1 | 10/2002 | Blair et al. |
| 6,472,398 | B1 | 10/2002 | Palucki et al. |
| 6,486,165 | B2 | 11/2002 | Zhang et al. |
| 6,515,122 | B1 | 2/2003 | Lang et al. |
| 6,531,476 | B1 | 3/2003 | Heymans et al. |
| 6,534,503 | B1 | 3/2003 | Dines et al. |
| 6,534,509 | B1 | 3/2003 | Bauman et al. |
| 6,555,537 | B2 | 4/2003 | Bauman et al. |
| 6,569,861 | B2 | 5/2003 | Bakthavatchalam et al. |
| 6,579,968 | B1 | 6/2003 | Blood et al. |
| 6,612,805 | B2 | 9/2003 | Rietsch |
| 6,648,848 | B1 | 11/2003 | Keldmann et al. |
| 6,673,767 | B1 | 1/2004 | Brodbeck et al. |
| 6,699,873 | B1 | 3/2004 | Maguire et al. |
| 6,715,485 | B1 | 4/2004 | Djupesland |
| 6,734,175 | B2 | 5/2004 | Hadcock et al. |
| 6,811,543 | B2 | 11/2004 | Keldmann et al. |
| 6,949,552 | B2 | 9/2005 | Nakazato et al. |
| 7,326,707 | B2 | 2/2008 | Sharma et al. |
| 7,354,923 | B2 | 4/2008 | Sharma et al. |
| 7,456,184 | B2 | 11/2008 | Sharma et al. |
| 2001/0018075 | A1 | 8/2001 | Shigeyuki et al. |
| 2001/0047001 | A1 | 11/2001 | Varkhedkar et al. |
| 2002/0004512 | A1 | 1/2002 | Bakshi et al. |
| 2002/0010182 | A1 | 1/2002 | Masaaki et al. |
| 2002/0019523 | A1 | 2/2002 | Palucki et al. |
| 2002/0022620 | A1 | 2/2002 | Kahn et al. |
| 2002/0032238 | A1 | 3/2002 | Priepke et al. |
| 2002/0037837 | A1 | 3/2002 | Takada et al. |
| 2002/0042399 | A1 | 4/2002 | Kruse et al. |
| 2002/0052383 | A1 | 5/2002 | Bakthavatchalam et al. |
| 2002/0065277 | A1 | 5/2002 | Hadcock et al. |
| 2002/0065416 | A1 | 5/2002 | Stasiak et al. |
| 2002/0072604 | A1 | 6/2002 | Carpino et al. |
| 2002/0082263 | A1 | 6/2002 | Lou et al. |
| 2002/0107253 | A1 | 8/2002 | Koh et al. |
| 2002/0107255 | A1 | 8/2002 | Blumberg et al. |
| 2002/0128247 | A1 | 9/2002 | Dow et al. |
| 2002/0128270 | A1 | 9/2002 | Neya et al. |
| 2002/0137664 | A1 | 9/2002 | Bakshi et al. |
| 2002/0143141 | A1 | 10/2002 | Chen et al. |
| 2002/0173512 | A1 | 11/2002 | Moltzen et al. |
| 2002/0177598 | A1 | 11/2002 | Bauman et al. |
| 2002/0183316 | A1 | 12/2002 | Pan et al. |
| 2003/0004162 | A1 | 1/2003 | Treadway |
| 2003/0013721 | A1 | 1/2003 | Meghani et al. |
| 2003/0040520 | A1 | 2/2003 | Guzi et al. |
| 2003/0055008 | A1 | 3/2003 | Marcotte |
| 2003/0055009 | A1 | 3/2003 | Steiner et al. |
| 2003/0055247 | A1 | 3/2003 | Cosford et al. |
| 2003/0055265 | A1 | 3/2003 | Binggeli et al. |
| 2003/0060473 | A1 | 3/2003 | Neya et al. |
| 2003/0064921 | A1 | 4/2003 | Millhauser et al. |
| 2003/0069169 | A1 | 4/2003 | Macor et al. |
| 2003/0083228 | A1 | 5/2003 | Carpino et al. |
| 2003/0083335 | A1 | 5/2003 | Hayward |
| 2003/0092732 | A1 | 5/2003 | Yu et al. |
| 2003/0096827 | A1 | 5/2003 | Yu et al. |
| 2003/0105106 | A1 | 6/2003 | Chiang et al. |
| 2003/0109556 | A1 | 6/2003 | Mazur et al. |
| 2003/0125334 | A1 | 7/2003 | Chiang et al. |
| 2003/0139425 | A1 | 7/2003 | Bauman et al. |
| 2003/0144277 | A1 | 7/2003 | DeLucca |
| 2003/0149019 | A1 | 8/2003 | Bremberg et al. |
| 2003/0158205 | A1 | 8/2003 | Bauman et al. |
| 2003/0158209 | A1 | 8/2003 | Dyck et al. |
| 2003/0162819 | A1 | 8/2003 | Eisinger et al. |
| 2003/0166637 | A1 | 9/2003 | Lehmann-Lintz et al. |
| 2003/0176425 | A1 | 9/2003 | Eisinger et al. |
| 2003/0181441 | A1 | 9/2003 | Mcclure et al. |
| 2003/0191136 | A1 | 10/2003 | Bakthavatchalam et al. |
| 2003/0195212 | A1 | 10/2003 | Lundstedt et al. |
| 2004/0006067 | A1 | 1/2004 | Fotsch et al. |
| 2004/0024211 | A1 | 2/2004 | Boyce et al. |
| 2004/0034034 | A1 | 2/2004 | Blumberg et al. |
| 2004/0053933 | A1 | 3/2004 | Pontillo et al. |
| 2004/0147567 | A1 | 7/2004 | Nakazato et al. |
| 2004/0152534 | A1 | 8/2004 | Chapman et al. |
| 2004/0157264 | A1 | 8/2004 | Sharma et al. |
| 2004/0171520 | A1 | 9/2004 | Sharma et al. |
| 2004/0204398 | A1 | 10/2004 | Bakshi et al. |
| 2004/0224957 | A1 | 11/2004 | Sharma et al. |
| 2004/0254198 | A1 | 12/2004 | Reynolds et al. |
| 2005/0124636 | A1 | 6/2005 | Sharma et al. |
| 2005/0130988 | A1 | 6/2005 | Sharma et al. |
| 2005/0176728 | A1 | 8/2005 | Sharma et al. |
| 2006/0009456 | A1 | 1/2006 | Hutchinson et al. |
| 2006/0084657 | A1 | 4/2006 | Nakazato et al. |
| 2006/0287330 | A1 | 12/2006 | Sharma et al. |
| 2006/0287331 | A1 | 12/2006 | Sharma et al. |
| 2006/0287332 | A1 | 12/2006 | Sharma et al. |
| 2008/0070921 | A1 | 3/2008 | Burris et al. |
| 2008/0234289 | A1 | 9/2008 | Sharma et al. |
| 2009/0076029 | A1 | 3/2009 | Sharma et al. |
| 2009/0081197 | A1 | 3/2009 | Burris et al. |

FOREIGN PATENT DOCUMENTS

| | | |
|---|---|---|
| WO | WO 97/46553 | 12/1997 |
| WO | WO 98/10653 | 3/1998 |
| WO | WO 98/17625 | 4/1998 |
| WO | WO 99/55679 | 11/1999 |
| WO | WO 99/58501 | 11/1999 |
| WO | WO 99/64002 | 12/1999 |
| WO | WO 00/01726 | 1/2000 |
| WO | WO 00/05373 | 2/2000 |
| WO | WO 00/17348 | 3/2000 |
| WO | WO 00/35952 | 6/2000 |
| WO | WO 00/36136 | 6/2000 |
| WO | WO 00/40247 | 7/2000 |
| WO | WO 00/53148 | 9/2000 |
| WO | WO 00/68185 | 11/2000 |
| WO | WO 00/74679 | 12/2000 |
| WO | WO 01/05401 | 1/2001 |
| WO | WO 01/10842 | 2/2001 |
| WO | WO 01/12176 | 2/2001 |

| | | |
|---|---|---|
| WO | WO 01/13112 | 2/2001 |
| WO | WO 01/18210 | 3/2001 |
| WO | WO 01/21634 | 3/2001 |
| WO | WO 01/21647 | 3/2001 |
| WO | WO 01/23392 | 4/2001 |
| WO | WO 01/30343 | 5/2001 |
| WO | WO 01/30808 | 5/2001 |
| WO | WO 01/35970 | 5/2001 |
| WO | WO 01/52880 | 7/2001 |
| WO | WO 01/55106 | 8/2001 |
| WO | WO 01/55107 | 8/2001 |
| WO | WO 01/55109 | 8/2001 |
| WO | WO 01/70708 | 9/2001 |
| WO | WO 01/91752 | 12/2001 |
| WO | WO 02/00259 | 1/2002 |
| WO | WO 02/00654 | 2/2002 |
| WO | WO 02/12178 | 2/2002 |
| WO | WO 02/15909 | 2/2002 |
| WO | WO 02/18437 | 3/2002 |
| WO | WO 02/47670 | 6/2002 |
| WO | WO 02/059095 | 8/2002 |
| WO | WO 02/059107 | 8/2002 |
| WO | WO 02/059108 | 8/2002 |
| WO | WO 02/059117 | 8/2002 |
| WO | WO 02/062766 | 8/2002 |
| WO | WO 02/064091 | 8/2002 |
| WO | WO 02/064734 | 8/2002 |
| WO | WO 02/067869 | 9/2002 |
| WO | WO 02/068387 | 9/2002 |
| WO | WO 02/068388 | 9/2002 |
| WO | WO 02/069905 | 9/2002 |
| WO | WO 02/070511 | 9/2002 |
| WO | WO 02/079146 | 10/2002 |
| WO | WO 02/079203 | 10/2002 |
| WO | WO 02/079753 | 10/2002 |
| WO | WO 02/081443 | 10/2002 |
| WO | WO 02/085925 | 10/2002 |
| WO | WO 02/092566 | 11/2002 |
| WO | WO 03/006620 | 1/2003 |
| WO | WO 03/007949 | 1/2003 |
| WO | WO 03/009847 | 2/2003 |
| WO | WO 03/009850 | 2/2003 |
| WO | WO 03/013509 | 2/2003 |
| WO | WO 03/013571 | 2/2003 |
| WO | WO 03/020724 | 3/2003 |
| WO | WO 03/027239 | 4/2003 |
| WO | WO 03/031410 | 4/2003 |
| WO | WO 03/045920 | 6/2003 |
| WO | WO 03/053927 | 7/2003 |
| WO | WO 03/055477 | 7/2003 |
| WO | WO 03/061660 | 7/2003 |
| WO | WO 03/066587 | 8/2003 |
| WO | WO 03/066597 | 8/2003 |
| WO | WO 03/072056 | 9/2003 |
| WO | WO 03/092690 | 11/2003 |
| WO | WO 03/093234 | 11/2003 |
| WO | WO 03/094918 | 11/2003 |
| WO | WO 2004/037796 | 5/2004 |
| WO | WO 2005/102340 | 11/2005 |
| WO | WO 2006/014552 | 2/2006 |
| WO | WO 2007/021990 | 2/2007 |
| WO | WO 2007/021991 | 2/2007 |

OTHER PUBLICATIONS

Hruby VJ, Al-obeidi F and Kazmierski W: *Biochem J* 268:249-262, 1990.
Toniolo C: *Int J Peptide Protein Res* 35:287-300, 1990.
Sasaki S et al., Discovery of a Thieno[2,3-*d*]pyrimidine-2,4-dione bearing a *p*-methoxyureidophenyl moiety at the 6-position: a highly potent and orally bioavailable non-peptide antagonist for the human luteinizing hormone-releasing hormone receptor. *J. Med. Chem.* 46:113-124 (2003).
Cho N et al., Discovery of a novel, potent, and orally active nonpeptide antagonist of the human luteinizing hormone-release hormone (LHRH) receptor. *J. Med. Chem.* 41:4190-4195 (1998).
U.S. Appl. No. 11/110,060, filed Apr. 19, 2005, Sharma et al.
U.S. Appl. No. 12/130,299, filed May 30, 2008, Burris et al.
U.S. Appl. No. 12/130,316, filed May 30, 2008, Sharma et al.
Abou-Gharbia et al. "Synthesis and SAR or Adatanserin: Novel Adamantyl Aryl- and Heteroarylpiperazines with Dual Serotonin -5HT$_{1A}$ and 5-HT$_2$ Activity as Potential Anxiolytic and Antidepressant Agents" J. Med. Chem. 42(25):5077-5094 (1999).
Adan et al. "Identification of antagonists for melanocortin MC3, MC4 and MC5 receptors" Eur. J. Pharmacol. 269(3):331-337 (1994).
Adan et al. "Inverse agonism gains weight" Trends in Pharmacological Sciences 24(6):315-321 (2003).
Alterman et al. "Design and synthesis of new potent C2-symmetric HIV-1 protease inhibitors. Use of L-mannaric acid as a peptidomimetic scaffold" J. Med. Chem. 41:3782-3792 (1998).
Baldwin et al. "Synthesis of a bicyclic γ-lactam dipeptide analogue" Tetrahedron Letters 34(10):1665-1668 (1993).
Chang et al. "Morphiceptin (NH4-tyr-pro-phe-pro-COHN2): a potent and specific agonist for morphine (mu) receptors" Science 212(4490):75-77 (1981).
Chorev et al. "Toward nonpeptidal substance P mimetic analogues: Design, synthesis, and biological activity" Biopolymers 31(6):725-733 (1991).
Cornille et al. "Anodic amide oxidations: Conformationally restricted peptide building blocks from the direct oxidation of dipeptides" Tetrahedron Letters 35(38):6989-6992 (1994).
DiMaio et al. "Synthesis of chiral piperazin-2-ones as model peptidomimetics" J Chem. Soc., Perkin Trans I, 1687-1689 (1989).
Dorr et al. "Evaluation of melanotan-II, a superpotent cyclic melanotropic peptide in a pilot phase-I clinical study" Life Science 58(20):1777-1784 (1996).
Gante "Peptidomimetics—Tailored enzyme-inhibitors" Angewandte Chemie International Edition in English 33(17):1699-1720 (1994).
Giannis et al. "Peptidomimetics in drug design" Advances in Drug Research 29:1-78 (1997).
Hadley et al. "Discovery and development of novel melanogenic drugs. Melanotan-I and -II" Ronald. T. Borchardt, et al. editors; Integration of Pharmaceutical Discovery and Development: Case Histories, Plenum Press, New York, 575-595 (1998).
Haskell-Luevano et al. "Discovery of Prototype Peptidomimetic Agonists at the Human Melanocortin Receptors MC1R and MC4R"J. Med. Chem. 40:2133-2139 (1997).
Hruby et al. "Molecular organization of receptors—Efficacy, agonists, and antagonists" Annals of the New York Academy of Sciences 757:7-22 (1995).
Jones et al. "Clinically validated peptides as templates for de novo peptidomimetic drug design at G-protein coupled receptors" Current Opinion in Pharmacology 3:530-543 (2003).
Kask et al. "Discovery of a novel superpotent and selective melanocortin-4 receptor antagonist (HS024): Evaluation in vitro and in vivo" Endocrinology 139(12):5006-5014 (1998).
Kim et al. "Synthesis of (3R)-carboxy pyrrolidine (a β-proline analogue) and its oligomer" Bioorganic & Medicinal Chemistry Letters 10(21):2417-2419 (2000).
Klein et al. "O-benzyl hydroxyproline as a bioisostere for Phe-Pro: Novel dipeptide thrombin inhibitors"Bioorganic & Medicinal Chemistry Letters 6(18):2225-2230 (1996).
Lerner et al. "Synthetic melanocortin receptor. Agonist and antagonists" Cutaneous Neuroimmunomodulation: The Proopiomelanocortin System, Annals of the New York Academy of Sciences 885:153-160 (1995).
Medicial Encyclopaedia: Female sexual dysfuntion [online]. Retrieved on Oct. 10, 2007 from http://www.nlm.nih.gov/medlineplus/ency/article/003151.htm.
Mitsunobu "The use of diethyl azodicarboxylate and triphenylphosphine in synthesis and transformation of natural products" Synthesis 1:1-28 (1981).
Moore et al. "A rapid screening system to determine drug affinities for the instestinal dipeptide transporter 2: Affinities of ACE inhibitors" International Journal of Pharmaceutics 210: 29-44 (2000).

Moore et al. "Designing Peptide Mimetics" Trends Pharmacol. Sci. 15:124-129 (1994).

Rarey et al. "Similarity searching in large combinatorial chemsitry spaces" J. Computer-Aided Mol. Des. 15(6):497-520 (2001).

Rubsam et al. "Synthesis of chiral piperazinones as versatile scaffolds for peptidomimetics" Tetrahedron 56(43):8481-8487 (2000).

Schioth et al. "Pharmacological comparison of rat and human melanocortin 3 and 4 receptors in vitro" Regulatory Peptides 106:7-12 (2002).

Shvachkin et al. "Synthesis of analogs of the thyrotropin-releasing hormone" Journal of General Chemistry of the USSR in English Translation 43(3):686-687 (1973).

Stavropoulos et al. "Synthesis of cis-4-hydroxy-L-proline and its incorporation into biologically important peptides" Review of Clinical Pharmacology and Pharmacokinetics 103-106 (1995).

Sudoh et al. "Transport characteristics of peptidomimetics. Effect of the pyrrolinone bioisostere of transport across caco-2 cell monolayers" Pharmaceutical Research 15(5):719-725 (1998).

Takenaka et al. "Synthesis of met- and leu-enkephalin analogues containing chiral N,N-ethylene-bridged phenylalanyl-methionine and -leucine" J Chem. Soc., Perkin Trans I, 8:933-937 (1993).

Torres et al. "Neoglycopeptide synthesis and purification in multigram scale: preparation of O-(2,3,4,6-tetra-O-acetyl-beta-D-galactopyranosyl)-N alpha-fluoren-9-yl-methoxycarbonyl-hydroxyproline and its use in the pilot-scale synthesis of the potent analgesic glycopeptide O1.5-beta-D-galactopyranosyl [DMet2, Hyp5]enkephalinamide." Journal of Peptide Science 3(2):99-109 (1997).

Torres et al. "Synthesis and conformational analysis of a series of galactosyl enkephalin analogues showing high analgesic activity" The EMBO Journal 8(10):2925-2932 (1989).

Yamamoto "Synthesis and adhesive studies of marine polypeptides" J. Chem. Soc., Perkin Trans I, 3:613-618 (1987).

Zhorov et al. "Similarity of Ca2+-bound conformations of morphine and Met-enkephalin: A computational study" FEBS Letters 354(2):131-134 (1994).

Cachexia [online], retrieved on Nov. 19, 2009 from the internet (URL: http://en.wikipedia.org/wiki/Cachexia).

Inui "Cancer anorexia-cachexia syndrome: Current issues in research and management" CA A Cancer Journal for Clinicians 52:72-91 (2002).

Fan et al. "Role of melanocortinergic neurons in feeding and the agouti obesity syndrome" Nature 385(6612):165-168 (1997).

Holder et al. "Melanocortin ligands: 30 years of structure-activity relationship (SAR) studies" Medicinal Research Reviews 24(3): 325-356 (2004).

Hruby et al. "Synthesis of oligopeptide and peptidomimetic libraries" Current Opinion in Chemical Biology 1(1): 114-119 (1997).

THIENO [2,3-D]PYRIMIDINE-2,4-DIONE MELANOCORTIN-SPECIFIC COMPOUNDS

CROSS-REFERENCE TO RELATED APPLICATIONS

This application is a continuation-in-part application of U.S. patent application Ser. No. 10/762,079, entitled "piperazine Melanocortin-Specific Compounds", filed on Jan. 21, 2004, which claimed priority to U.S. Provisional Patent Application Ser. No. 60/474,497, entitled "Substituted piperazine Compounds Specific for Melanocortin Receptors", filed on May 30, 2003 and U.S. Provisional Patent Application Ser. No. 60/441,139, entitled "Ring Core Compounds Specific for Melanocortin Receptors", filed on Jan. 17, 2003, and which in turn was a continuation-in-part application of International Application No. PCT/US02/25574, International Publication No. WO 03/013571, entitled "Peptidomimetics of Biologically Active Metallopeptides", filed on Aug. 12, 2002, which claimed priority to U.S. Provisional Patent Application Ser. No. 60/311,404, entitled "Receptor-Specific Peptides Derived from Biologically Active Metallopeptides", filed on Aug. 10, 2001. This application is also a continuation-in-part application of U.S. patent application Ser. No. 10/761,889, entitled "Bicyclic Melanocortin-Specific Compounds", filed on Jan. 21, 2004, which claimed priority to U.S. Provisional Patent Application Ser. No. 60/441,139, entitled "Ring Core Compounds Specific for Melanocortin Receptors", filed on Jan. 17, 2003, and which in turn was a continuation-in-part application of International Application No. PCT/US02/25574, International Publication No. WO 03/013571, entitled "Peptidomimetics of Biologically Active Metallopeptides", filed on Aug. 12, 2002, which claimed priority to U.S. Provisional Patent Application Ser. No. 60/311,404, entitled "Receptor-Specific Peptides Derived from Biologically Active Metallopeptides", filed on Aug. 10, 2001. This application is also a continuation-in-part application of U.S. patent application Ser. No. 10/837,519, entitled "Melanocortin Receptor-Specific Compounds", filed on Apr. 30, 2004, which claimed priority to U.S. Provisional Patent Application Ser. No. 60/546,393, entitled "Melanocortin Receptor-Specific Tetra-Substituted piperazine Compounds", filed on Feb. 19, 2004, and U.S. Provisional Patent Application Ser. No. 60/467,442, entitled "Tetra-, Penta- and Hexa-Substituted piperazine Compounds and Derivatives", filed on May 1, 2003. The specification of each of the foregoing patent applications, including international applications and provisional applications, is incorporated herein by reference.

This application claims the benefit of the filing of U.S. Provisional Patent Application Ser. No. 60/538,100, entitled "Thieno[2,3-d]pyrimidine-2,4-dione Melanocortin-Specific Compounds", filed on Jan. 21, 2004, and the specification thereof is incorporated herein by reference.

BACKGROUND OF THE INVENTION

1. Field of the Invention (Technical Field)

The present invention relates to small molecules, and in particular thienopyrimidine bicyclic ring core structure small molecules wherein one ring member is sulfur and two ring members are nitrogen, which bind to one or more melanocortin receptors, may be agonists, antagonists or mixed agonist-antagonists, and have utility for the treatment of melanocortin receptor-associated disorders.

2. Description of Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R) expressed primarily in cells in the hypothalamus, midbrain and brainstem, and melanocortin-5 receptors (MC5-R), expressed in a wide distribution of tissues.

In general, compounds specific for MC1-R are believed to be useful for treatment of melanoma. Compounds specific for MC3-R or MC4-R are believed to be useful in regulation of energy homeostasis, including use as agents for attenuating food intake and body weight gain, for use in treatment of anorexia, as a weight gain aid, for treatment of obesity, and other treatment of other food intake and metabolism-related purposes. Compounds specific for MC3-R and MC4-R, among other melanocortin receptors, can be used as agents for treatment of sexual dysfunction, including male erectile dysfunction. Other melanocortin receptor-specific compounds, such as MCR-1 agonists, can be used as tanning agents to increase melanin production. Compounds specific for MCR-1 and MCR-3 may be useful in regulation of inflammatory processes.

There are thienopyrimidine compounds with pendant aromatic groups that are known, such as those disclosed in U.S. Pat. No. 6,340,868 and U.S. patent application Ser. No. 2004/0254198. However, these compounds are asserted to be antagonists for gonadotropin releasing hormone in the case of U.S. Pat. No. 6,340,868, and useful for autoimmune disease in the case of U.S. patent application Ser. No. 2004/0254198. There are no described thienopyrimidine compounds that are specific for one or more melanocortin receptors, or which are either agonists or antagonists with respect to one or more melanocortin receptors.

There is a significant need for compounds with high specificity for discrete melanocortin receptors, as well as compounds that are either agonists or antagonists for specific melanocortin receptors. High affinity compounds for melanocortin receptors can be used to exploit varied physiological responses associated with the melanocortin receptors, as agonists, antagonists, inverse agonists, antagonists of inverse agonists or low or functionally inactive compounds. In addition, melanocortin receptors have an effect on the activity of various cytokines, and high affinity compounds for melanocortin receptors can be used to regulate cytokine activity.

BRIEF SUMMARY OF THE INVENTION

In one embodiment, the invention provides a thienopyrimidine compound of the formula:

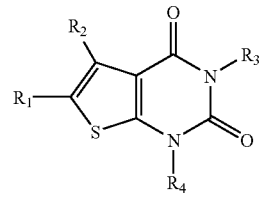

or an enantiomer, stereoisomer or diastereoisomer thereof, or a pharmaceutically acceptable salt thereof,
wherein
$R_1$ is -$L_1$-J;
$R_2$ is -$L_2$-W;
$R_3$ is -$L_3$-T
$R_4$ is -$L_4$-Q;

$L_1$ is a bond or a linker unit comprising from one to eight backbone atoms selected from the group consisting of carbon, sulfur, oxygen or nitrogen;

J is a carbocyclic ring group comprising at least one aromatic ring;

$L_2$ is $—(CX)_m—$;

W is ring structure selected from the group consisting of substituted or unsubstituted aromatic carbocyclic rings, substituted or unsubstituted non-aromatic carbocyclic rings, substituted or unsubstituted aromatic fused carbobicyclic ring groups, two substituted or unsubstituted aromatic carbocyclic rings wherein the rings are joined by a bond or —O—, and substituted or unsubstituted aromatic fused heterobicyclic ring groups; wherein in each instance the rings include 5 or 6 ring atoms;

$L_3$ and $L_4$ are $—(CH_2)_m—$;

T is a heteroatom unit with at least one cationic center wherein at least one heteroatom is nitrogen or oxygen;

Q is a carbocyclic ring group comprising at least one aromatic ring;

X is at each occurrence independently H, $H_2$, or a $C_1$ to $C_{12}$ linear or branched alkyl; and y is at each occurrence independently from 1 to 6.

In the compounds, T may be $—NH_2$, N(Z)(Z), $—NH—C(=NH)—NH_2$ or $—N(Z)-C(=N(Z))-N(Z)(Z)$, where each Z is independently H or $CH_3$. Thus $R_3$ may be

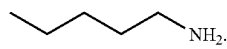

In one embodiment, at least one aromatic ring of J or Q, or both, is functionalized with one or more halogen, alkyl or aryl groups. Preferably Q does not comprise 2,6-difluorobenzyl.

In a particularly preferred embodiment, $R_1$ is:

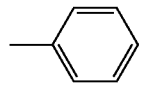

$R_2$ is:

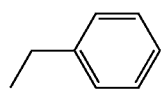

$R_3$ is:

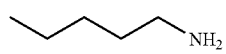

and $R_4$ is:

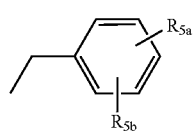

wherein $R_{5a}$ and $R_{5b}$ are optional ring substituents, and when one or both are present, are the same or different and independently hydroxyl, halogen, alkyl, or aryl groups attached directly or through an ether linkage, but excluding fluorine (F) in the 2 and 6 position.

The foregoing compounds are preferably specific for one or more melanocortin receptors, and may be antagonists, inverse agonists, agonists or partial agonists at one or more melanocortin receptors.

The invention further provides a pharmaceutical composition for treatment of a melanocortin receptor-associated disorder, comprising the foregoing compound and a pharmaceutically acceptable carrier. The invention thus encompasses a method for treatment of a melanocortin receptor-associated disorder, comprising administration of a therapeutically effective amount of a pharmaceutical composition. The melanocortin receptor-associated disorder may be sexual dysfunction or an energy homeostasis disorder.

The invention further provides a method for treatment of a melanocortin receptor-associated disorder, comprising administration of a therapeutically effective amount of a compound of the formula:

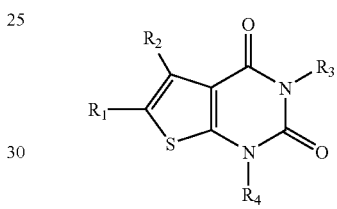

or an enantiomer, stereoisomer or diastereoisomer thereof, or a pharmaceutically acceptable salt thereof, wherein $R_1$ is $-L_1-J$;

$R_2$ is $-L_2-W$;

$R_3$ is $-L_3-T$ $R_4$ is $-L_4-Q$;

$L_1$ is a bond or a linker unit comprising from one to eight backbone atoms selected from the group consisting of carbon, sulfur, oxygen or nitrogen;

J is a carbocyclic ring group comprising at least one aromatic ring;

$L_2$ is a bond or $—(CX)_m—$;

W is $Y_n$, where each Y is independently $N(CH_3)_2$, NH, N, $CH_2$, or C=O and n has a value between 1 and 8, provided that any 5 or more Y units can be taken together to form an aromatic or non-aromatic carbocyclic or heterocyclic ring;

$L_3$ and $L_4$ are a bond or $—(CH_2)_m—$;

T is a ring structure selected from the group consisting of substituted or unsubstituted aromatic carbocyclic rings, substituted or unsubstituted aromatic fused carbobicyclic ring groups, or two substituted or unsubstituted aromatic carbocyclic rings wherein the rings are joined by a bond or —O—, wherein in each instance the rings include 5 or 6 ring atoms;

Q is a carbocyclic ring group comprising at least one aromatic ring;

X is at each occurrence independently H, $H_2$, or a $C_1$, to $C_{12}$ linear or branched alkyl; and m is at each occurrence independently from 1 to 6.

Thus in the practice of the method $L_2$ may be —$(CH_2)_m$— and W may be $N(CH_3)_2$, for example wherein $R_2$ is

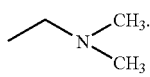

In the practice of the method, at least one aromatic ring of J or Q, or both, may be functionalized with one or more halogen, alkyl or aryl groups, and in a preferred embodiment, wherein Q does not comprise 2,6-difluorobenzyl.

In the practice of the method, $R_1$ and $R_3$ may be:

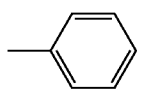

$R_2$ may be:

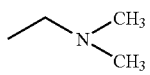

and $R_4$ may be:

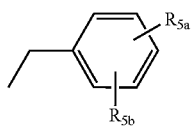

wherein $R_{5a}$ and $R_{5b}$ are optional ring substituents, and when one or both are present, are the same or different and independently hydroxyl, halogen, alkyl, or aryl groups attached directly or through an ether linkage, but excluding F in the 2 and 6 position.

In the practice of the method, the compound is preferably specific for one or more melanocortin receptors, and may be an antagonist, inverse agonist, antagonist of an inverse agonist, agonist or partial agonist at one or more melanocortin receptors.

In one embodiment the present invention provides a thienopyrimidine compound that is an agonist of a melanocortin receptor, including MC1-R, MC3-R, MC4-R, or MC5-R.

In another embodiment, the present invention provides a thienopyrimidine compound that is an antagonist of a melanocortin receptor, including MC1-R, MC3-R, MC4-R, or MC5-R.

In another embodiment, the present invention provides a thienopyrimidine compound that is an inverse agonist of a melanocortin receptor, including MC1-R, MC3-R, MC4-R, or MC5-R.

In another embodiment, the present invention provides a thienopyrimidine compound that is an antagonist of an inverse agonist, such as agouti-related protein (AgRP), of a melanocortin receptor, including MC4-R.

In another embodiment, the present invention provides a thienopyrimidine compound which binds to one more melanocortin receptors, and competes with one or more melanocortin receptor binding agents in a competitive inhibition assay, but which has low functional activity or is functionally inactive with little or no intrinsic activity at the receptor.

In one embodiment of the invention there is provided a method of treating obesity or feeding-related disorders, the method including administration of a therapeutically effective amount of a thienopyrimidine compound of the invention wherein the compound binds to the melanocortin 4 receptor with high affinity.

The invention further includes a method for altering a disorder or condition associated with the activity of a melanocortin receptor, comprising administering to a patient a therapeutically effective amount of a thienopyrimidine compound of this invention. In one embodiment the disorder or condition is an eating disorder such as cachexia. In another embodiment the disorder or condition is obesity and associated impairment of energy homeostasis. In another embodiment the disorder or condition is sexual dysfunction.

A primary object of the present invention is to provide thienopyrimidine core compounds or derivatives thereof, wherein pendant group substituents are amino acid moieties, amino acid side chain moieties or derivatives thereof, such that the resulting compound biologically mimics a relevant reverse turn peptide structure that is characteristic of melanocortin peptides.

Another object of the present invention is to provide thienopyrimidine compounds and derivatives thereof.

Another object of the present invention is to provide thienopyrimidine compounds and derivatives of thienopyrimidine compounds with at least four pendant groups, such pendant groups consisting of any moiety other than H, O, S, or a halogen.

Another object of the present invention is to provide thienopyrimidine compounds or derivatives thereof wherein such compounds are specific for one or more melanocortin receptors.

Another object of the present invention is to provide methods for synthesis of thienopyrimidine compounds.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the compounds, formulas, instrumentalities and combinations particularly pointed out in the appended claims.

DETAILED DESCRIPTION OF THE INVENTION

In one embodiment, the invention comprises a 5,6-membered bicyclic ring compound of the formula:

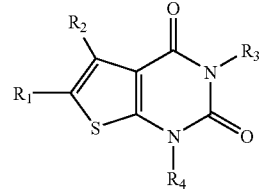

wherein $R_1$, $R_2$, $R_3$, and $R_4$ are any moiety as shown in Table 1 or Table 2.

In a further embodiment:

$R_1$ comprises any moiety comprising an aromatic carbocyclic ring;

$R_2$ comprises —$C(X)_n$—$Y_m$, where each X is independently H, $H_2$ or $C_1$, to $C_{12}$ linear or branched alkyl, n has a value between 1 and 6, each Y is independently —N(CH$_3$)$_2$, —NH, —N, CH$_2$, or C=O, and m has a value between 1 and 8, provided that any 5 or more Y units can be taken together to form an aromatic or non-aromatic carbocyclic or heterocyclic ring;

R$_3$ is any moiety comprising an aromatic carbocyclic ring or a C$_1$ to C$_{12}$ linear or branched alkyl, optionally with a terminal —NH$_2$; and R$_4$ comprises an aromatic carbocyclic ring, said ring optionally functionalized with one or more halogen, alkyl or aryl groups.

Any of the aromatic carbocyclic rings at R$_1$, R$_2$, R$_3$, or R$_4$ may be all or part of an amino acid side chain or derivative of an amino acid side chain containing an aromatic carbocyclic ring, including without limitation any of the amino acid residues listed herein that include one or more aromatic carbocyclic rings.

Definitions. Before proceeding further with the description of the invention, certain terms are defined as set forth herein.

The terms "amino acid" and "amino acids" as used in the specification include the known naturally occurring protein amino acids, which are referred to by both their common three letter abbreviation and single letter abbreviation. See generally *Synthetic Peptides: A User's Guide*, GA Grant, editor, W.H. Freeman & Co., New York, 1992, the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V J, Al-obeidi F and Kazmierski W: *Biochem J* 268:249-262,1990; and Toniolo C: *Int J Peptide Protein Res* 35:287-300, 1990; the teachings of all of which are incorporated herein by reference.

The term "amino acid side chain moiety" used in this invention, including as used in the specification, includes any side chain of any amino acid, as the term "amino acid" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition.

The "derivative" of an amino acid side chain moiety includes any modification to or variation in any amino acid side chain moieties, including a modification of naturally occurring amino acid side chain moieties. By way of example, derivatives of amino acid side chain moieties include straight chain or branched, cyclic or noncyclic, substituted or unsubstituted, saturated or unsaturated, alkyl, aryl or aralkyl moieties. Derivatives of amino acid side chain moieties further include amino acid side chain moieties, preferably amino acid side chain moieties with a functional group, the amino acid side chain moieties further including one or more protecting groups, preferably an orthogonal protecting group.

The following abbreviations for amino acids, amino acid side chain moieties and derivatives and constituents thereof have the meanings giving, it being understood that any amino acid may be in either the L- or D-configuration. Amino acid side chains, including derivatives of amino acid side chains, of any of the following amino acids may be employed in the practice of the invention for any pendent group including one or more aromatic or carbocyclic rings:

| | |
|---|---|
| Achc | 1-amino-cyclohexane-1-carboxylic acid |
| Acpc | 1-amino-cyclopropane-1-carboxylic acid |
| Amc | 4-(aminomethyl)-cyclohexane carboxylic acid |
| Beta-hHyp(Bzl) | beta-(O-benzyl)-homohydroxyproline |
| Beta-hSer(Bzl) | beta-(O-benzyl)-homoserine |
| Bip | biphenylalanine |
| Cha | cyclohexylalanine |
| Chg | cyclohexylglycine |
| Cys(Bzl) | S-benzyl-cysteine |
| Hyp(Bzl) | O-benzyl-hydroxyproline |
| Hyp(2-naphthly) | O-2' naphthyl-hydroxyproline |
| Hyp(Phenyl) | O-phenyl-hydroxyproline |
| Nal 1 | 3-(1-naphthyl)alanine |
| Nal 2 | 3-(2-naphthyl)alanine |
| (N-Bzl)Nal 2 | N-benzyl-3-(2-naphthyl) alanine |
| (N-PhEt)Nal 2 | N(2-phenylethyl)-3-(2-naphthyl) alanine |
| Phg | phenylglycine |
| Phe(4-F) | para-fluoro-phenylalanine |
| Phe(4-Br) | 4-bromo-phenylalanine |
| Phe(4-CF$_3$) | 4-trifluoromethyl-phenylalanine |
| Phe(4-Cl) | 4-chloro-phenylalanine |
| Phe(3-Cl) | 3-chloro-phenylalanine |
| Phe(2-Cl) | 2-chloro-phenylalanine |
| Phe(2,4-diCl) | 2,4,-dichloro-phenylalanine |
| Phe(2,4-diF) | 2,4-difluoro-phenylalanine |
| Phe(3,4-diCl) | 3,4,-dichloro-phenylalanine |
| Phe(5-Cl) | 5-chloro-phenylalanine |
| Phe(2-Cl,4-Me) | 2-chloro-4-methyl-phenylalanine |
| Phe(2-Me,4-Cl) | 4-chloro-2-methyl-phenylalanine |
| Phe(2-F,4-Cl) | 4-chloro-2-fluoro-phenylalanine |
| Phe(2,4-diMe) | 2,4-dimethyl-phenylalanine |
| Phe(2-Cl,4-CF$_3$) | 2-chloro-4-trifluoromethyl-phenylalanine |
| Phe(3,4-diF) | 3,4,-difluoro-phenylalanine |
| Phe(4-I) | 4-iodo-phenylalanine |
| Phe(3,4-di-OMe) | 3,4,-dimethoxy-phenylalanine |
| Phe(4-Me) | 4-methyl-phenylalanine |
| Phe(4-OMe) | 4-methoxy-phenylalanine |
| Phe(4-NC) | 4-cyano-phenylalanine |
| Phe(4-NO$_2$) | 4-nitro-phenylalanine |
| 4-phenylPro | 4-phenyl-pyrrolidin-2-carboxylic acid |
| 5-phenylPro | 5-phenyl-pyrrolidin-2-carboxylic acid |
| Ser(Bzl) | O-benzyl-serine |
| Ser(2-Naphthyl) | O-2-Naphthyl-serine |
| Ser(Phenyl) | O-2-Phenyl-serine |
| Ser(4-Cl-Phenyl) | O-4-Cl-Phenyl-serine |
| Ser(2-Cl-Phenyl) | O-2-Cl-Phenyl-serine |
| Ser(p-Cl-Bzl) | O-4-Cl-Benzyl-serine |
| Thr(Bzl) | O-Benzyl-threonine |
| Thr(2-Naphthyl) | O-(2-naphthyl)-threonine |
| Thr(Phenyl) | O-phenyl-threonine |
| Thr(4-Cl-Phenyl) | O-(4-Cl-phenyl)-threonine |
| Thr(2-Cl-Phenyl) | O-(2-Cl-phenyl)-threonine |
| Beta-homoThr(Bzl) | O-Benzyl-beta-homothreonine |
| Tyr(Bzl) | O-benzyl-tyrosine |
| Tyr(2,6-DiCl-Bzl) | O-(2,6 dichloro)benzyl-tyrosine |

Conventional amino acid residues have their conventional meaning as given in Chapter 2400 of the *Manual of Patent Examining Procedure*, 8$^{th}$ Ed. Thus, "His" is histidine, "D-Phe" is D-phenylalanine, "Arg" is arginine, "Trp" is tryptophan, "Tyr" is tyrosine, "Ser" is serine and so on.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "alkynal" includes a linear monovalent hydrocarbon radical of two to six carbon atoms or a branched monovalent hydrocarbon radical of three to six carbon atoms containing at least one triple bond; examples thereof include ethynyl, propynal, butynyl, and the like.

The term "aryl" includes a monovalent or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical —$R^a R^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

The term "acyl" includes a group RCO—, where R is an organic group. An example is the acetyl group $CH_3CO$—.

A group or aliphatic moiety is "acylated" when an alkyl or substituted alkyl group as defined above is bonded through one or more carbonyl {—(C=O)—} groups.

An "omega amino derivative" includes an aliphatic moiety with a terminal amino group. Examples of omega amino derivatives include aminoheptanoyl and the amino acid side chain moieties of ornithine and lysine.

The term "heteroaryl" includes mono- and bicyclic aromatic rings containing from 1 to 4 heteroatoms selected from nitrogen, oxygen and sulfur. 5- or 6-membered heteroaryls are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

An "amide" includes compounds that have a trivalent nitrogen attached to a carbonyl group (—$CO.NH_2$), such as methylamide, ethylamide, propylamide, and the like.

An "imide" includes compounds containing an imido group (—CO.NH.CO—).

An "amine" includes compounds that contain an amino group (—$NH_2$).

A "nitrile" includes compounds that are carboxylic acid derivatives and contain a (—CN) group bound to an organic group.

An amino acid side chain moiety is "hydrogen bonding" when the side chain includes hydrogen donors or alternatively hydrogen acceptors.

The term "halogen" is intended to include the halogen atoms fluorine, chlorine, bromine and iodine, and groups including one or more halogen atoms, such as —$CF_3$ and the like.

By a melanocortin receptor "agonist" is meant an endogenous or drug substance or compound, including a compound of this invention, that can interact with a melanocortin receptor and initiate a pharmacological response, including but not limited to adenyl cyclase expression, characteristic of a melanocortin receptor. By a melanocortin receptor "antagonist" is meant a drug or a compound, including a compound of this invention, that opposes the melanocortin receptor-associated responses normally induced by a melanocortin receptor agonist agent, but without itself initiating a pharmacological response characteristic of a melanocortin receptor, such as increasing or decreasing adenyl cyclase expression. By a melanocortin receptor "inverse agonist" is meant a drug or a compound, including a compound of this invention, which is an antagonist with respect to an agonist, and which by itself induces or initiates a pharmacological response characteristic of a melanocortin receptor, such as reducing basal or constitutive adenyl cyclase expression.

By "binding affinity" is meant the ability of a compound or drug to bind to its biological target.

By "intrinsic activity" is meant the maximal stimulation of adenyl cyclase achievable by a compound in a melanocortin receptor cell system. The maximal stimulation achieved by α-MSH or NDP-α-MSH is designated as an intrinsic activity of 1.0 (or 100%) and a compound capable of stimulating half the maximal activity that of α-MSH or NDP-α-MSH is designated as having an intrinsic activity of 0.5 (or 50%). A compound of this invention that under assay conditions described herein has an intrinsic activity of 0.7 (70%) or higher is classified as an agonist, a compound with intrinsic activity between 0.1 (10%) and 0.7 (70%) is classified as a partial agonist, and a compound with intrinsic activity below 0.1 (10%) is classified as inactive or having no intrinsic activity. Compounds with intrinsic activity below 0.1 (10%) can be further evaluated for antagonist effect.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and one or more pharmaceutically acceptable carriers, and optionally one or more pharmaceutically active ingredients and agents.

A variety of chemicals and compounds are employed in this invention, and the following abbreviations have the meanings given:

| | |
|---|---|
| AIBN | 2,2'-azobisisobutyronitrile |
| AcOH | acetic acid |
| DCM | dichloromethane |
| DMF | N,N-dimethylformamide |
| NBS | N-bromosuccinimide |
| TEA | triethylamine |
| TFA | trifluoroacetic acid |

"Sexual dysfunction" means any condition that inhibits or impairs normal sexual function, including coitus. The term is not limited to physiological conditions, and includes psychogenic conditions or perceived impairment without a formal diagnosis of pathology or disorder. Sexual dysfunction includes erectile dysfunction in a male mammal and female sexual dysfunction in a female mammal.

"Erectile dysfunction" is a disorder involving the failure of a male mammal to achieve functional erection, ejaculation, or both. Erectile dysfunction is accordingly synonymous with impotence, and includes the inability to attain or sustain an erection of sufficient rigidity for coitus. Symptoms of erectile dysfunction include an inability to achieve or maintain an erection, ejaculatory failure, premature ejaculation, or inability to achieve an orgasm. An increase in erectile dysfunction is often associated with age or may be caused by a physical disease or as a side-effect of drug treatment.

"Female sexual dysfunction" is a disorder including sexual arousal disorder. The term "sexual arousal disorder" includes a persistent or recurrent failure to attain or maintain the lubrication-swelling response of sexual excitement until completion of sexual activity. Sexual dysfunction in females can also include inhibited orgasm and dyspareunia, which is painful or difficult coitus. Female sexual dysfunction includes, but is not limited to, a number of categories of diseases, conditions and disorders including hypoactive sexual desire disorder, sexual anhedonia, sexual arousal disorder, dyspareunia and vaginismus. Hypoactive sexual desire disorder includes a disorder in which sexual fantasies and desire for sexual activity are persistently or recurrently diminished or absent, causing marked distress or interpersonal difficulties. Hypoactive sexual desire disorder can be caused by boredom or unhappiness in a long-standing relationship, depression, dependence on alcohol or psychoactive drugs, side effects from prescription drugs, or hormonal deficiencies. Sexual anhedonia includes decreased or absent pleasure in sexual activity. Sexual anhedonia can be caused by depression, drugs, or interpersonal factors. Sexual arousal disorder can be caused by reduced estrogen, illness, or treatment with diuretics, antihistamines, antidepressants, or antihypertensive agents. Dyspareunia and vaginismus are sexual pain disorders characterized by pain resulting from penetration and may be caused, for example, by medications which reduce lubrication, endometriosis, pelvic inflammatory disease, inflammatory bowel disease or urinary tract problems.

Formulation and Utility

The compounds may be synthesized by the methods and synthetic schemes hereafter described. In general, the compounds of this invention may be synthesized in part, such as for specific reactions or synthetic steps, by synthetic schemes, and further may be purified, according to methods known in the art. Of particular utility are the methods disclosed in Sasaki S et al., Discovery of a Thieno[2,3-d]pyrimidine-2,4-dione bearing a p-methoxyureidophenyl moiety at the 6-position: a highly potent and orally bioavailable non-peptide antagonist for the human luteinizing hormone-releasing hormone receptor. *J. Med. Chem.* 46:113-124 (2003) and Cho N et al., Discovery of a novel, potent, and orally active nonpeptide antagonist of the human luteinizing hormone-release hormone (LHRH) receptor. *J. Med. Chem.* 41:4190-4195 (1998), both of which are incorporated here by reference. Any of a number of known procedures utilizing a variety of reagents may be employed at various steps in the synthesis of the compounds of this invention.

Clinical Applications. Melanocortin receptor-specific compounds of this invention that are MC1-R specific can be used as chemoprevention agents against sun-induced, such as by UV radiation, neoplastic activity in human skin. MC1-R agonist compounds of this invention may be employed to stimulate epidermal melanocytes to produce melanin as well as to convert pheomelanin to eumelanin. Eumelanin, which is dark brown or black pigmentation, is considered more photoprotective than pheomelanin, which is yellow or red pigmentation. The process of melanogenesis is believed to involve stimulation of MC1-R in epidermal melanocytes, thereby mediating the stimulation of tyrosinase enzymes within these pigment cells, inducing the conversion of tyrosine to dopa and then through dopaquinone to eumelanin. Sun tanning due to direct sun exposure is proposed to result from the same pathway by local production of melanotropic peptide from a POMC gene in the epidermis. Thus stimulation of eumelanin production and conversion of pheomelanin to eumelanin may be a desirable chemoprevention modality in blocking sun- or UV-induced neoplastic activity in skin. A potent, high-affinity and highly selective MC1-R agonist compound of this invention can accordingly be used as a therapeutic chemoprevention agent for combating harmful sun or UV exposure that induces neoplastic activity in skin melanocytes.

In another embodiment compounds of this invention that are MC4-R agonists can be used as a therapeutic agent to modify energy metabolism and feeding behavior, including treatment of pathologic obesity and related conditions. Compounds of this invention that are MC4-R antagonists can also be used as a therapeutic agent in eating disorders, such as treatment of anorexia or cachexia. Control centers for eating and satiety reside in the hypothalamus. These responses are determined by diverse hormones and soluble factors that signal through specific receptors in the hypothalamus. MC4-R is known to be expressed in the brain, and inactivation of this receptor by gene targeting has resulted in mice with the maturity-onset obesity syndrome that is associated with hyperphagia, hyperinsulinemia and hyperglycemia.

In yet another embodiment, compounds of this invention may be used as therapeutic agents for treatment of sexual dysfunction, including treatment of both male erectile dysfunction and female sexual dysfunction. In yet another embodiment, compounds of this invention may be used as therapeutic agents for treatment of inflammation, including specifically MC1-R and MC3-R agonists.

In yet another embodiment of the invention, compounds of this invention that are MC5-R specific can be used as agents to decrease sebum production, and thus may be efficacious in the treatment of acne and related diseases. The compounds for this application may be conveniently formulated for local administration, as through a gel, lotion, cream or other topical formulation.

The methods, compounds and pharmaceutical compositions of this invention can be used for both medical applications and animal husbandry or veterinary applications. Typically, the compound or pharmaceutical composition is used in humans, but may also be used in other mammals, particular farm or sport animals. The term "patient" is intended to denote a mammalian individual, and is so used throughout the specification and in the claims. While one primary application of this invention involves human patients, another primary application of the invention involves animals, particularly laboratory, farm, zoo, wildlife, pet, sport or other animals.

Salt Form of Compounds. The compounds of this invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the compounds of this invention are prepared in a suitable solvent from the compound and an excess of an acid, such as hydrochloric, hydrobromic, sulfuric, phosphoric, acetic, trifluoroacetic, citric, tartaric, maleic, succinic or methanesulfonic acid. The acetate salt form is especially useful. Where the compounds of this invention include an acidic moiety, suitable pharmaceutically acceptable salts may include alkali metal salts, such as sodium or potassium salts, or alkaline earth metal salts, such as calcium or magnesium salts.

Pharmaceutical Compositions. The invention provides a pharmaceutical composition that includes a compound of this invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

The compositions of this invention may be formulated or compounded into pharmaceutical compositions that include at least one compound of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, mannitol, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a compound of this invention over a period of time.

In practical use, the compounds of the invention can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Because of their ease of administration, tablets and capsules represent an advantageous oral dosage unit form. If desired, tablets may be coated by standard aqueous or non-aqueous techniques. The amount of active compound in such therapeutically useful compositions is such that an effective dosage will be obtained. In another advantageous dosage unit form, sublingual constructs may be employed, such as sheets, wafers, tablets or the like. The compounds can also be administered intranasally as, for example, by liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch or alginic acid; a lubricant such as magnesium stearate; and a sweetening agent such as sucrose, lactose or saccharin. When a dosage unit form is a capsule, it may contain, in addition to materials of the above type, a liquid carrier such as fatty oil.

Various other materials may be utilized as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds may also be administered parenterally. Solutions or suspensions of compounds can be prepared in water suitably mixed with a surfactant such as hydroxy-propylcellulose. Dispersions can also be prepared in glycerol, liquid polyethylene glycols and mixtures thereof in oils. These preparations may optionally contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

The compounds of this invention may be therapeutically applied by means of nasal administration. By "nasal administration" is meant any form of intranasal administration of any of the compounds of this invention. The compounds may be in an aqueous solution, such as a solution including saline, citrate or other common excipients or preservatives. The compounds may also be in a dry or powder formulation.

In an alternative embodiment, compounds of this invention may be administered directly into the lung. Intrapulmonary administration may be performed by means of a metered dose inhaler, a device allowing self-administration of a metered bolus of a compound of this invention when actuated by a patient during inspiration.

Routes of Administration. If it is administered by injection, the injection may be intravenous, subcutaneous, intramuscular, intraperitoneal or other means known in the art. The compounds of this invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the compounds of invention are introduced across an epidermal layer of cells may be employed. Administration means may thus include administration through mucous membranes, buccal administration, oral administration, dermal administration, inhalation administration, nasal administration, urethral administration, vaginal administration, and the like.

Therapeutically Effective Amount. In general, the actual quantity of compound of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. Thus a therapeutically effective amount includes an amount of a compound or pharmaceutical composition of this invention that is sufficient to modulate energy homeostasis, such as by increasing or decreasing food intake and/or increasing or decreasing body weight, preferably over a determined period of time. Similarly, a therapeutically effective amount includes an amount of a compound or pharmaceutical composition of this invention that is sufficient to induce a sexual response, including inducing a penile erection in a male mammal.

In general, the compounds of this invention are highly active, with dose responses as low as 0.1 µg/Kg, and optimal or peak dose responses between about 0.1 µg/Kg and 25 µg/Kg, depending on the specific compound and the route of administration. For example, the compound can be administered at 0.01, 0.05, 0.1, 0.5, 1, 5, 10, 50, 100, or 500 µg/Kg body weight, depending on specific compound selected, the desired therapeutic response, the route of administration, the formulation and other factors known to those of skill in the art. Conventional dose response studies and other pharmacological means may be employed to determine the optimal dose for a desired effect with a given compound, given formulation and given route of administration. This may readily be determined by one of ordinary skill in the art through means such as pharmacokinetic studies, plasma half-life studies, dose escalation studies, and the like.

Melanocortin Receptor Binding Assays. A competitive inhibition binding assay can be employed to determine inhibition of binding of α-MSH or an α-MSH analog, such as by using membranes prepared from hMC3-R, hMC4-R, hMC5-R, and B-16 mouse melanoma cells (containing MC1-R) using 0.4 nM $^{125}$I-NDP-MSH (0.2 nM for MC1-R) (New England Nuclear, Boston, Mass., USA) in 50 mM HEPES buffer containing 1 mM $MgCl_2$, 2 mM $CaCl_2$, and 5 mM KCl, at pH 7.2. The assay tube contains a chosen concentration of the compound of this invention, most preferably 1 µM, for determining inhibition of the binding of $^{125}$I-NDP-MSH to its receptor. Non-specific binding is measured by complete inhibition of binding of $^{125}$I-NDP-MSH in the assay in the presence of 1 µM α-MSH. Incubation is for 90 minutes at 37° C., after which the assay mixture is filtered and the membranes washed three times with ice cold buffer. The filter is dried and counted in a gamma counter for remaining radioactivity bound to the membranes. 100% specific binding is defined as the difference in radioactivity (cpm) bound to cell membranes in the absence and presence of 1 µM α-MSH. The cpm obtained in the presence of compounds of this invention is normalized with respect to 100% specific binding to determine the percent inhibition of $^{125}$I-NDP-MSH binding.

Functional assays to determine agonist or antagonist status of a compound may be conducted by any means known in the art. In one method, a cAMP assay is performed. Human MC4-R cells are grown to confluence in 96 well plates (plating approximately 250,000 cells per well). Identical sets of cells in triplicate are treated with 0.2 mM isobutylmethylxanthine (IBMX) and the chosen concentration of the compound or alternatively the compound in the presence of 20 nM NDP-MSH. Cells similarly treated but with only 20 nM NDP-MSH serve as positive control. A buffer blank, as a negative control, is also included. Incubation is for one hour at 37° C. after which the cells are lysed by the addition of 50 µL of a cell lysis buffer. Total cAMP accumulated in 250 µL of this solution is quantitated using a commercially available low pH cAMP assay kit (Amersham BioSciences) by the procedure specified by the kit supplier. Any test subject showing cAMP accumulation in the same range as or higher than the positive control (buffer blank in the presence of α-MSH) is considered to be an agonist. A test subject showing accumulation in the same range as the negative control (buffer blank in the absence of α-MSH) is ineffective at the test concentration if the result is similar to the positive control where α-MSH is also present in the assay. A test subject showing accumulation in the same range as the negative control is considered to be an antagonist if there is inhibition in cAMP when α-MSH is present in the assay. Similar methods may be employed for MC3-R, using MC3-R cells. Compounds of this invention are, in one particularly preferred embodiment, ineffective at any concentration, and thus are neither an agonist nor an antagonist with respect to MC4-R.

In a particularly preferred embodiment, certain of the compounds of the invention are specific for one or more melanocortin receptors, particularly MC3-R and/or MC4-R, such as determined by a competitive inhibition binding assay, and may be highly specific, such as inhibiting up to 100% of the binding of α-MSH or $^{125}$I-NDP-MSH or having a Ki (nM) of 10 or less, preferably 1 or less, at either or both MC3-R and MC4-R, and are effective for treatment of sexual dysfunction, but do not cause a biological response associated with activation or inhibition of a melanocortin receptor, such as at 1 µM concentration or lower, particularly MC3-R and/or MC4-R, and thus do not modulate feeding behavior in mammals or elicit or cause other responses characteristic of MC4-R specific molecules, including without limitation treatment of obesity or diabetes mellius such as associated with MC3-R or MC4-R specific agonists, or treatment of cachexia or wasting disease associated with cancer, AIDS, failure to thrive syndrome, and diseases associated with aging and senility such as associated with MC4-R specific antagonists.

In another particularly preferred embodiment, certain of the compounds of the invention cause a biological response associated with activation or inhibition of a melanocortin receptor, such as at 1 µM concentration or lower, particularly MC3-R and/or MC4-R, and thus may be employed to modulate feeding behavior in mammals or elicit or cause other responses characteristic of MC4-R specific molecules, including without limitation treatment of obesity or diabetes mellius such as associated with MC3-R or MC4-R specific agonists, or treatment of cachexia or wasting disease associated with cancer, AIDS, failure to thrive syndrome, and diseases associated with aging and senility such as associated with MC4-R specific antagonists.

The invention is further illustrated by the following non-limiting examples.

EXAMPLE 1

Competitive Inhibition Assays

A competitive inhibition binding assay is conducted using membranes prepared from hMC3-R, hMC4-R, hMC5-R, and B-16 mouse melanoma cells (containing MC1-R) using 0.4 nM $^{125}$I-NDP-α-MSH (New England Nuclear, Boston, Mass., USA) in 50 mM HEPES buffer containing 1 mM $MgCl_2$, 2 mM $CaCl_2$, and 5 mM KCl, at pH 7.2. The assay tube also contains a chosen concentration of the test compound of this invention, preferably a concentration of 1 µM, for determining its efficacy in inhibiting the binding of $^{125}$I-NDP-α-MSH to its receptor. Non-specific binding is measured by complete inhibition of binding of $^{125}$I-NDP-α-MSH in the assay with the presence of 1 µM α-MSH.

Incubation is for 90 minutes at room temperature, after which the assay mixture was filtered and the membranes washed three times with ice cold buffer. The filter is dried and counted in a gamma counter for remaining radioactivity bound to the membranes. 100% specific binding is defined as the difference in radioactivity (cpm) bound to cell membranes in the absence and presence of 1 µM α-MSH. The cpm obtained in presence of test compounds are normalized with respect to 100% specific binding to determine the percent inhibition of $^{125}$I-NDP-α-MSH binding. Each assay is conducted in triplicate and the actual mean values are described.

EXAMPLE 2

Functional Evaluation at Melanocortin Receptors

Functional evaluation of compounds at melanocortin receptors is performed by measuring the accumulation of intracellular cAMP in HEK-293 cells expressing MC3-R, MC4-R or MC5-R, and in B-16 mouse melanoma cells (containing MC1-R). Cells, suspended in Earle's Balanced Salt Solution containing 10 mM HEPES, pH 7.5, 5 mM $MgCl_2$, 1 mM glutamine, 0.1% albumin and 0.6 mM 3-isobutyl-1-methyl-xanthine, a phosphodiesterase inhibitor, are plated in 96 well plates at a density of $0.5 \times 10^5$ cells per well. Cells are incubated with the test compounds, preferably at a concentration of 1 µM, in the presence or absence of α-MSH for 1 hour at 37° C. cAMP levels are measured by EIA (Amersham) in the cell lysates. Data analysis and $EC_{50}$ values are determined using nonlinear regression analysis with Prism Graph-Pad software.

EXAMPLE 3

Agonist/Antagonist Status

The agonist/antagonist status with respect to MC4-R of compounds of the invention is determined. Antagonistic activity is determined by measuring the inhibition of α-MSH-induced cAMP levels following exposure to the compounds as in Example 2.

EXAMPLE 4

Evaluation for Sexual Dysfunction

The ability of compounds to induce penile erection (PE) in male rats is evaluated with selected compounds. Male Sprague-Dawley rats weighing 200-250 g are kept on a 12 hour on/off light cycle with food and water ad libitum. All behavioral studies are performed between 10 a.m. and 5 p.m. Groups of 4-8 rats are treated with compounds at a variety of doses via intravenous (IV) or intracerebroventricular (ICV) routes. Immediately after treatment, rats are placed into individual polystyrene cages (27 cm long, 16 cm wide, and 25 cm high) for behavioral observation. Rats are observed for 30 minutes (for IV treated rats) or 120 minutes (for ICV treated rats) and the number of yawns, grooming bouts and PEs are recorded in 10-minute bins.

EXAMPLE 5

Food Intake and Body Weight

Change in food intake and body weight are evaluated for selected compounds. Male Sprague-Dawley rats weighing ~300 g at the beginning of the experiment are kept on a 12 hour on/off light cycle. Lights out is adjusted to 12:00 p.m. to allow for dosing just prior to the start of their dark period. Rats (8-12/group) were fed powdered chow and water ad libitum. For 1 week before treatment, 24-hour food intake and body weight change is recorded to assess a baseline for the group during vehicle treatment. The rats are dosed ICV with vehicle or selected compounds (1-3 nmol) or IV with vehicle or selected compounds (0.5-3 mg/kg). The changes in body weight and food intake for the 24 hour period after dosing are determined. The changes in body weight and food intake for the 48 hour period, and in some cases the 72 hour period, after dosing is also measured to determined reversal of changes in body weight and food intake effect back to baseline.

EXAMPLE 6

Synthesis of Thieno[2,3-d]pyrimidine-2,4-dione Compounds

5-,6-membered bicyclic ring core compounds are made as set forth in Scheme 1. The compounds of this example have the following general formula, with variable assignments as given in Table 1:

TABLE 1

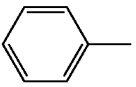

| No. | R₁ | R₂ | R₃ | R₄ |
|---|---|---|---|---|
| 1 |  | 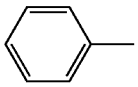 | 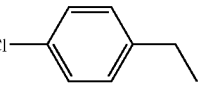 | 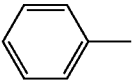 |
| 2 |  | 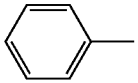 | 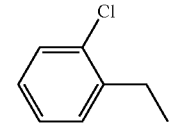 | 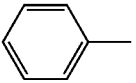 |
| 3 |  | 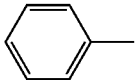 |  | |

To make the compounds of Example 6, a mixture of ketone (1 equivalent), ethyl cyanoacetate (1 equivalent), ammonium acetate (0.2 equivalent) and acetic acid (0.8 equivalent) is refluxed in toluene for 20 hours with a Dean-Stark apparatus. The mixture is concentrated. The residue is diluted with saturated sodium hydrogen carbonate and extracted with chloroform. The organic layer is washed with brine and dried over magnesium sulfate. After evaporation of solvent the residue is purified on silica gel column. This purified compound is dissolved in ethanol. To this solution is added sulfur powder (1 equivalent) and diethylamine (1 equivalent). The solution is stirred at 65° C. for 2 hours. The solvent is removed and the residue is diluted with brine and extracted with chloroform. The extract is washed with brine and dried over magnesium sulfate. The solution is concentrated and residue is purified on a silica gel column or recrystallized from a suitable solvent to give compound A.

A mixture of compound A and a desired isocyanate (1.2 equivalent) in pyridine is stirred at 45° C. for 2 hours. After removal of solvent the residue is suspended in methanol and sodium methoxide (2.5 equivalent) is added. The mixture is stirred at room temperature for 6 hours and acidified with 2 N hydrochloric acid at 0° C. The solvent is removed and the precipitates (B) are collected. After washing with water, compound B is dried under vacuum.

A mixture of compound B, substituted benzyl chloride (1.2 equivalent), potassium carbonate (1.5 equivalent) and potassium iodide (0.5 equivalent) in DMF is stirred at room temperature for 4 hours. The solvent is removed and the residue is partitioned between chloroform and water. The aqueous phase is extracted with chloroform. The combined organic phase is washed with brine and dried over magnesium sulfate. After removal of solvent the residue is recrystallized from a suitable solvent to give compound C.

A mixture of compound C, N-bromosuccinimide (1.2 equivalent) and 2,2'-azobisisobutyronitrile (0.12 equivalent) in chlorobenzene is stirred at 90° C. for 1.5 hours. The mixture is cooled to room temperature and concentrated. The residue is diluted with water and extracted with methylene chloride. The extract is washed with brine and dried over magnesium sulfate. The solvent is removed to give a crude bromomethyl compound. To a mixture of this bromomethyl compound and N,N-diisopropylethylamine (1.3 equivalent) in DMF is added dimethylamine (2.0 M in THF, 1.2 equivalent) After being stirred for 2 hours, the solvent is evaporated. The residue is purified on silica gel column to give compound D.

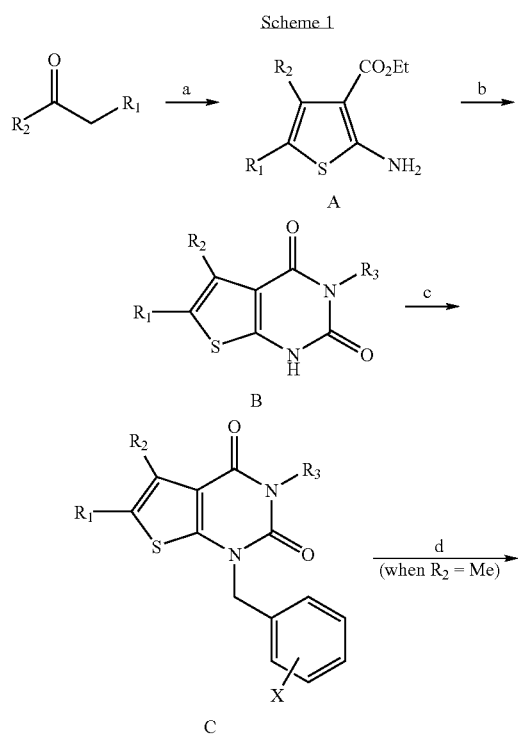

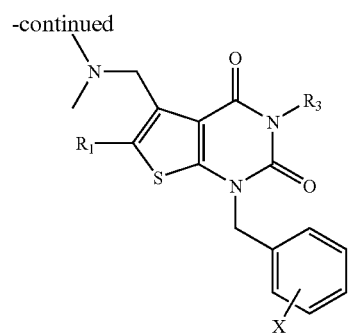

Reagents:
(a) i) ethyl cyanoacetate, AcNH$_4$, AcOH, toluene, ii) sulfur powder, Et$_2$NH, EtOH;
(b) i) R$_3$NCO, pyridine, ii) NaOMe, MeOH;
(c) X-substituted benzylchloride, K$_2$CO$_3$, KI, DMF;
(d) i) NBS, AIBN, chlorobenzene, ii) HNMe$_2$, K$_2$CO$_3$, DMF.

EXAMPLE 7

Alternative Synthesis of Thieno[2,3-d]pyrimidine-2,4-dione Compounds

5-,6-membered bicyclic ring core compounds are made as set forth in Scheme 2. The compounds of this example have the following general formula, with variable assignments as given in Table 2:

TABLE 2

| No. | R$_1$ | R$_2$ | R$_3$ | R$_4$ |
|---|---|---|---|---|
| 4 | biphenyl-CH$_2$- | H$_2$N-(CH$_2$)$_4$- | 4-Cl-benzyl |  |
| 5 | biphenyl-CH$_2$- | H$_2$N-(CH$_2$)$_4$- | 2-Cl-benzyl |  |
| 6 | biphenyl-CH$_2$- | H$_2$N-(CH$_2$)$_4$- | 4-CH$_3$-benzyl |  |

To make the compounds of Example 7, the general methods of Scheme 2 are employed. The synthetic methodology utilizes a suitable ketone to provides $R_1$ and $R_2$ groups in the final compound (such as 1,2-diphenyl-ethanone for compounds described in Table 2); a desired isocyanate $R_3$—NCO to provide for a $R_3$ group in the final compound (such as, 4-isocyanato-butyl-carbamic acid tert-butyl ester for compounds described in Table 2); and a substituted benzyl chloride to provide for a $R_4$ group in the final compound (such as 4-chloro-benzyl chloride, 2-chloro-benzyl chloride, or 4-methyl-benzyl chloride respectively for compounds 4, 5, and 6 in Table 2).

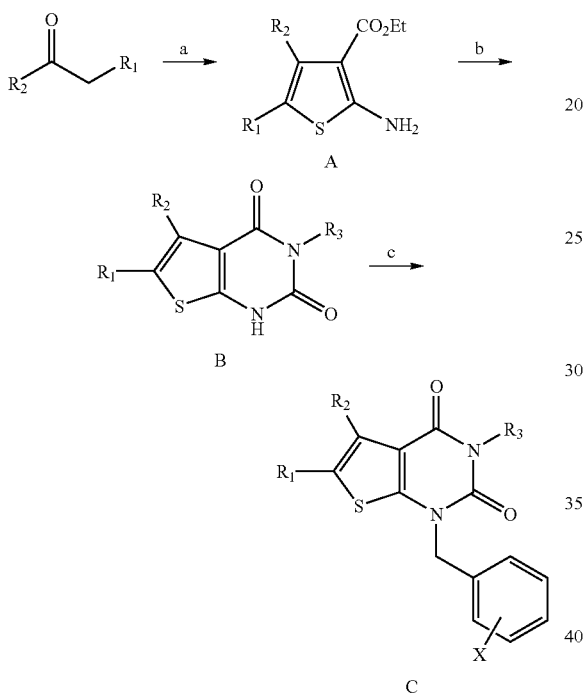

Reagents:
(a) i) ethyl cyanoacetate, AcNH$_4$, AcOH, toluene, ii) sulfur powder, Et$_2$NH, EtOH;
(b) i) R$_3$NCO, pyridine, ii) NaOMe, MeOH;
(c) i) X-substituted benzylchloride, K$_2$CO$_3$, KI, DMF; ii) TFA/DCM A mixture of ketone (1 equivalent), ethyl cyanoacetate (1 equivalent), ammonium acetate (0.2 equivalent) and acetic acid (0.8 equivalent) is refluxed in toluene for 20 hours with a Dean-Stark apparatus. The mixture is concentrated, residue diluted with saturated sodium hydrogen carbonate and extracted with chloroform. The organic layer is washed with brine and dried over magnesium sulfate. After evaporation of solvent the residue is purified on a silica gel column. This purified compound is dissolved in ethanol. To this solution is added sulfur powder (1 equivalent) and diethylamine (1 equivalent). The solution is stirred at 65° C. for 2 hours. The solvent is removed and the residue is diluted with brine and extracted with chloroform. The extract is washed with brine and dried over magnesium sulfate. The solution is concentrated and residue is purified on a silica gel column or recrystallized from a suitable solvent to give compound A.

A mixture of compound A and a desired isocyanate (1.2 equivalent) in pyridine is stirred at 45° C. for two hours. After removal of solvent the residue is suspended in methanol and sodium methoxide (2.5 equivalent) is added. The mixture is stirred at room temperature for 6 hours and acidified with 2 N hydrochloric acid at 0° C. The solvent is removed and the precipitates (B) are collected. After washing with water, compound B is dried under vacuum.

A mixture of compound B, substituted benzyl chloride (1.2 equivalent), potassium carbonate (1.5 equivalent) and potassium iodide (0.5 equivalent) in DMF is stirred at room temperature for 4 hours. The solvent is removed and the residue is partitioned between chloroform and water. The aqueous phase is extracted with chloroform. The combined organic phase is washed with brine and dried over magnesium sulfate. After removal of solvent the residue is recrystallized from a suitable solvent to give the product. This compound is subsequently treated with trifluoroacetic acid in methylene chloride for one hour. The solvent is removed and HPLC purification gives final compound C.

The preceding examples can be repeated with similar success by substituting the generically or specifically described pendant groups, structures, reactants and/or reaction conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A compound of the formula:

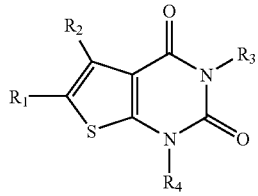

or an enantiomer, stereoisomer or diastereoisomer thereof, or a pharmaceutically acceptable salt thereof,
wherein
$R_1$ is -L$_1$-J;
$R_2$ is -L$_2$-W;
$R_3$ is -L$_3$-T;
$R_4$ is -L$_4$-Q;
L$_1$ is a bond or a linker unit comprising from one to eight backbone atoms selected from the group consisting of carbon, sulfur, oxygen and nitrogen;
J is a carbocyclic ring group comprising at least one aromatic ring;
L$_2$ is —(CX)$_m$—;
W is a ring structure selected from the group consisting of substituted or unsubstituted aromatic carbocyclic rings, substituted or unsubstituted non-aromatic carbocyclic rings, substituted or unsubstituted aromatic fused carbobicyclic ring groups, two substituted or unsubstituted aromatic carbocyclic rings wherein the rings are joined by a bond or —O—, and substituted or unsubstituted aromatic fused heterobicyclic ring groups; wherein in each instance the rings include 5 or 6 ring atoms;

L₃ and L₄ are —(CH₂)ₘ—;

T is —NH₂, N(Z)(Z), —NH—C(=NH)—NH₂ or —N(Z)—C(=N(Z))—N(Z)(Z), where each Z is independently H or CH₃;

Q is a carbocyclic ring group comprising at least one aromatic ring;

X is at each occurrence independently H, H₂, or a C₁ to C₁₂ linear or branched alkyl; and m is at each occurrence independently from 1 to 6.

2. The compound of claim 1 wherein R₃ is

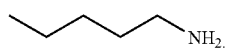

3. The compound of claim 1 wherein at least one aromatic ring of J or Q, or both, is substituted with one or more halogen, alkyl or aryl groups.

4. The compound of claim 2 wherein
R₁ is:

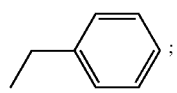

R₂ is:

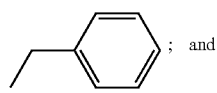
; and

R₄ is:

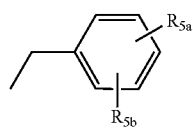

wherein R₅ₐ and R₅ᵦ are optional ring substituents, and when one or both are present, are the same or different and independently hydroxyl, halogen, alkyl, or aryl groups attached directly or through an ether linkage, but excluding F in the 2 and 6 position.

5. A pharmaceutical composition comprising a compound of claim 1 and a pharmaceutically acceptable carrier.

6. A method for treating a melanocortin receptor-associated disorder, comprising administering a therapeutically effective amount of a pharmaceutical composition of claim 5, wherein the melanocortin receptor-associated disorder is sexual dysfunction or an energy homeostasis disorder.

7. The method of claim 6 wherein the melanocortin receptor-associated disorder is cachexia.

8. The method of claim 6 wherein the melanocortin receptor-associated disorder is obesity.

9. A method for treating a melanocortin receptor-associated disorder, comprising administering a therapeutically effective amount of a compound of the formula:

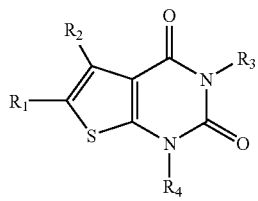

or an enantiomer, stereoisomer or diastereoisomer thereof, or a pharmaceutically acceptable salt thereof,
wherein
R₁ is -L₁-J;
R₂ is -L₂-W;
R₃ is -L₃-T
R₄ is -L₄-Q;
L1 is a bond or a linker unit consisting of from one to eight backbone atoms selected from the group consisting of carbon, sulfur, oxygen and nitrogen;
J is a carbocyclic ring group consisting of at least one aromatic ring;
L₂ is a bond or —(CX)ₘ—;
W is Yₙ, where each Y is independently N(CH₃)₂, NH, N, CH₂, or C=O and n has a value between 1 and 8, provided that any 5 or more Y units can be taken together to form an aromatic or non-aromatic carbocyclic or heterocyclic ring;
L₃ and L₄ are a bond or —(CH₂)ₘ—;
T is a ring structure selected from the group consisting of substituted or unsubstituted aromatic carbocyclic rings, substituted or unsubstituted aromatic fused carbobicyclic ring groups, and two substituted or unsubstituted aromatic carbocyclic rings wherein the rings are joined by a bond or —O—, wherein in each instance the rings include 5 or 6 ring atoms;
Q is a carbocyclic ring group consisting of at least one aromatic ring;
X is at each occurrence independently H, H₂, or a C₁ to C₁₂ linear or branched alkyl;
m is at each occurrence independently from 1 to 6; and
a pharmaceutically acceptable carrier,
wherein the melanocortin receptor-associated disorder is sexual dysfunction or an energy homeostasis disorder.

10. The method of claim 9 wherein L₂ is —(CH₂)ₘ— and W is N(CH₃)₂.

11. The method of claim 10 wherein R₂ is

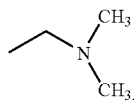

12. The method of claim 9 wherein at least one aromatic ring of J or Q, or both, is substituted with one or more halogen, alkyl or aryl groups.

13. The method of claim 11 wherein
R₁ and R₃ are:

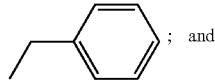
; and $R_4$ is:

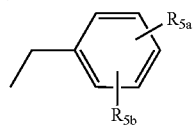

wherein $R_{5a}$ and $R_{5b}$ are optional ring substituents, and when one or both are present, are the same or different and independently hydroxyl, halogen, alkyl, or aryl groups attached directly or through an ether linkage, but excluding F in the 2 and 6 position.

14. The method of claim 9 wherein the melanocortin receptor-associated disorder is cachexia.

15. The method of claim 9 wherein the melanocortin receptor-associated disorder is obesity.

* * * * *

UNITED STATES PATENT AND TRADEMARK OFFICE
CERTIFICATE OF CORRECTION

| | | |
|---|---|---|
| PATENT NO. | : 7,655,658 B2 | Page 1 of 1 |
| APPLICATION NO. | : 11/040838 | |
| DATED | : February 2, 2010 | |
| INVENTOR(S) | : Shubh D. Sharma et al. | |

It is certified that error appears in the above-identified patent and that said Letters Patent is hereby corrected as shown below:

Claim 1, column 24, line 52, delete the word "comprising" and insert the words --consisting of--.

Claim 1, column 24, line 55, delete the word "comprising" and insert the words --consisting of--.

Claim 9, column 26, line 19, replace "L1" with --$L_1$--.

Signed and Sealed this

Thirteenth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,655,658 B2 Page 1 of 1
APPLICATION NO. : 11/040838
DATED : February 2, 2010
INVENTOR(S) : Sharma et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1024 days.

Signed and Sealed this

Twenty-third Day of November, 2010

David J. Kappos
*Director of the United States Patent and Trademark Office*